United States Patent
Schmitt

(10) Patent No.: US 10,422,772 B1
(45) Date of Patent: Sep. 24, 2019

(54) ACOUSTIC SENSING THROUGH A BARRIER

(71) Applicant: SONAVATION, INC., Palm Beach Gardens, FL (US)

(72) Inventor: Rainer M. Schmitt, Palm Beach Gardens, FL (US)

(73) Assignee: SONAVATION, INC., Palm Beach Gardens, FL (US)

( * ) Notice: Subject to any disclaimer, the term of this patent is extended or adjusted under 35 U.S.C. 154(b) by 81 days.

(21) Appl. No.: 15/299,202

(22) Filed: Oct. 20, 2016

Related U.S. Application Data

(60) Provisional application No. 62/244,102, filed on Oct. 20, 2015.

(51) Int. Cl.
*G01N 29/06* (2006.01)
*G01N 29/09* (2006.01)

(52) U.S. Cl.
CPC ......... *G01N 29/09* (2013.01); *G01N 29/0654* (2013.01); *G01N 2291/018* (2013.01)

(58) Field of Classification Search
CPC ............... G01N 29/09; G01N 29/0654; G01N 2291/018; G01S 7/52036; G01S 7/52038; G01S 7/52079; G01S 7/521; B06B 1/0607; G01H 15/00; A61B 8/4494; A61B 8/52

USPC .................. 73/589, 598, 617, 610–615, 644; 310/334

See application file for complete search history.

(56) References Cited

U.S. PATENT DOCUMENTS

| | | | |
|---|---|---|---|
| 9,841,318 B1* | 12/2017 | Schmitt | G01H 15/00 |
| 2005/0174015 A1 | 8/2005 | Scott | |
| 2010/0066207 A1 | 3/2010 | Saito | |
| 2015/0016223 A1* | 1/2015 | Dickinson | G06F 3/043 367/87 |
| 2016/0058417 A1* | 3/2016 | Kiyose | G01S 15/8925 600/472 |

OTHER PUBLICATIONS

Office Action dated Aug. 8, 2019 in U.S. Appl. No. 16/056,304.
Office Action dated Aug. 12, 2019 in U.S. Appl. No. 16/458,228.

* cited by examiner

*Primary Examiner* — Natalie Huls
*Assistant Examiner* — Suman K Nath
(74) *Attorney, Agent, or Firm* — Pillsbury Winthrop Shaw Pittman LLP

(57) ABSTRACT

The invention provides embodiments of an apparatus and for improved, higher quality and higher resolution acoustic impedance scanning of an object through a barrier. Such acoustic impedance scanning can be employed to obtain biometric information of a person via fingerprint pattern.

20 Claims, 5 Drawing Sheets

_US 10,422,772 B1_

ACOUSTIC SENSING THROUGH A BARRIER

This document is a Untied States Non-Provisional utility patent application under statue 35 U.S. C. 111(a).

CROSS REFERENCE TO RELATED PATENT APPLICATION(S)

This document is a United States (utility) Non-Provisional patent application that claims priority and benefit under 35 U.S.C. 119 (e) to U.S. (utility) provisional patent application having Ser. No. (62/244,102), that was filed on Oct. 20, 2015 and that is entitled "ACOUSTIC SENSING THROUGH A BARRIER", and which is incorporated herein by reference in its entirety.

DOCUMENTS INCLUDING RELATED SUBJECT MATTER

This patent application includes subject matter related to that included within U.S. Patent Publication No. 20100239133, which is entitled "Piezoelectric Identification Device and Applications Thereof" and was published on Sep. 23, 2010, and which was later issued as U.S. Pat. No. 8,508,103 on Aug. 13, 2013. A copy of this patent publication document is included within a prior filed provisional patent application, for which priority and benefit is herein claimed.

This patent application also includes subject matter related to that included within U.S. Patent Publication No. 20110010904, which is entitled "Method for Manufacturing a Piezoelectric Ceramic Body" and was published on Jan. 20, 2011, and which was later issued as U.S. Pat. No. 8,703,040 on Apr. 22, 2014.

This patent application also includes subject matter related to that included within U.S. patent application Ser. No. 14/464,956, which is entitled "Methods for Accurate Extraction of a Fingerprint Through a Barrier", that was filed on Aug. 21, 2014.

All of the above referenced documents are incorporated by reference herein in their entirety.

BACKGROUND OF THE INVENTION

In some circumstances, there exists a motivation to perform acoustic sensing (scanning) of a target through a barrier. For example, acoustic sensing of a fingerprint pattern, as a target, provides biometrical information of a person of interest. The barrier provides protection of a fingerprint pattern scanning sensor from wear and tear and possible damage resulting from physical contact between the sensor and objects outside of the sensor.

The discussion above is merely provided for general background information and is not intended to be used as an aid in determining the scope of the claimed subject matter.

BRIEF DESCRIPTION OF THE INVENTION

The invention provides apparatus, method and system embodiments for improved, higher quality and higher resolution acoustic impedance scanning of an object through a barrier. Such acoustic impedance scanning can be employed to obtain biometric information of a person via image capture of fingerprint pattern.

This brief description of the invention is intended only to provide a brief overview of subject matter disclosed herein according to one or more illustrative embodiments, and does not serve as a guide to interpreting the claims or to define or limit the scope of the invention, which is defined only by the appended claims.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its entire scope, for the entire scope of the invention can encompass other equally effective embodiments.

The drawings are not necessarily to scale. The emphasis of the drawings is generally being placed upon illustrating the features of certain embodiments of the invention. In the drawings, like numerals are used to indicate like parts throughout the various views. Differences between like parts may cause those parts to be indicated with different numerals. Unlike parts are indicated with different numerals. Thus, for further understanding of the invention, reference can be made to the following detailed description, read in connection with the drawings in which.

DETAILED DESCRIPTION OF THE INVENTION

Figure 1:
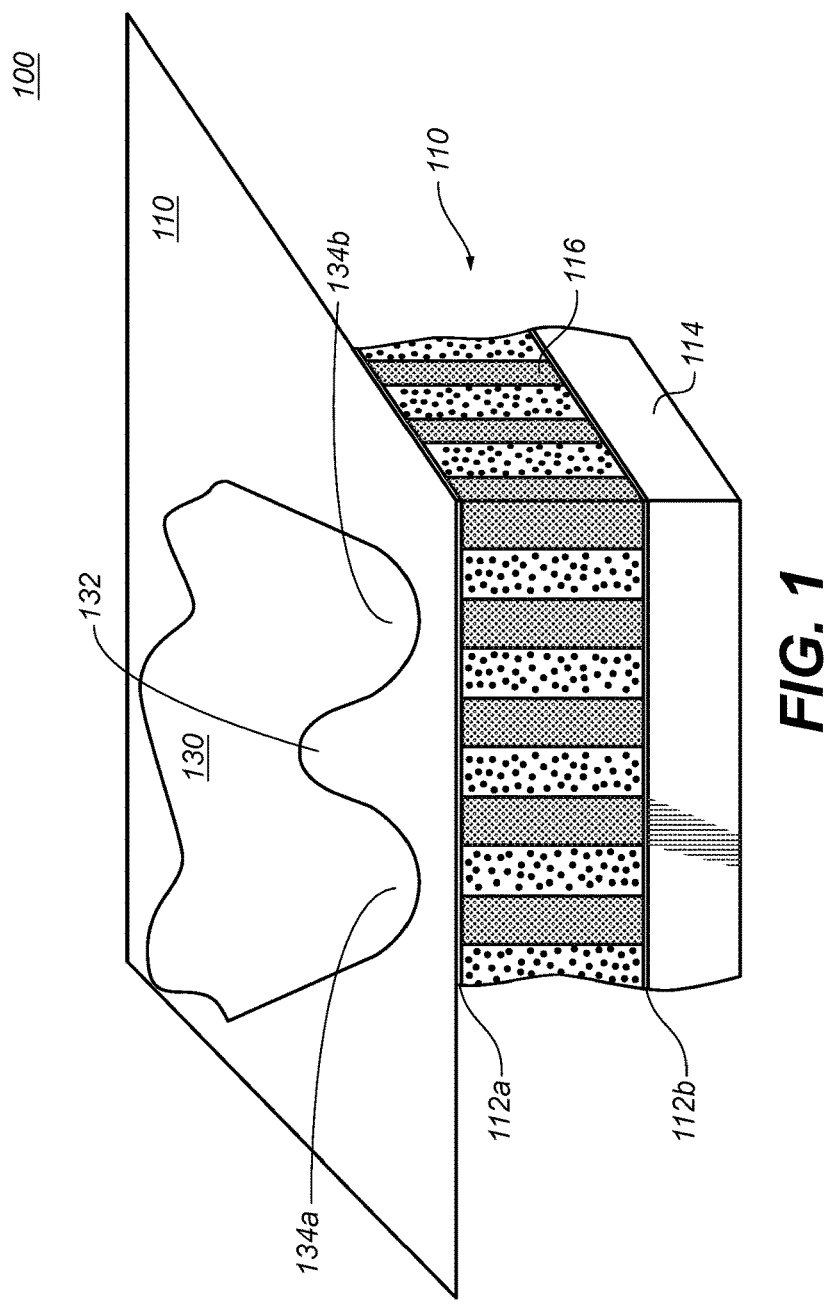
FIG. 1 illustrates an embodiment of an acoustic sensor that senses surface characteristics of a finger, while the finger is in direct physical contact with the sensor.

FIG. 1 illustrates an embodiment of an acoustic sensor 110 that senses characteristics of a finger 130, while the finger 130 is in direct physical contact with the sensor 110. The finger 130, also referred to herein as finger tissue 130, is shown to be in direct physical contact with the sensor 110. As shown, the acoustic impedance sensor 110, also referred to herein as the touch sensor 110 or sensor 110, is a device that is transmitting acoustic energy towards the finger 130.

In this circumstance, the finger 130 is in direct physical contact with an outer and upper surface of the sensor 110. This embodiment of the sensor 110 includes a matrix of vibrating pillars 116 that are each made from piezo-ceramic material. Interstitial filler material 118 abuts the pillars 116 and functions to reduce cross-talk (transfer) of motion and to reduce parasitic currents occurring between the pillars 116. The outer and upper surface of the acoustic sensor 110 is also an outer and upper surface of an upper protective layer 112a of the acoustic sensor 110. The upper protective layer 112a and the lower protective layer 112b are each a thin membrane that protects the matrix of vibrating pillars 116 within the sensor 112, from direct physical contact with finger tissue 130.

The transmission of acoustical energy from the sensor 110 via the vibrating pillars 116, also referred to herein as an acoustic energy (AE) transmission path, encounters acoustic impedance caused by the finger tissue 130, and encounters acoustic impedance caused by atmospheric air surrounding the finger 130. An insignificant amount of acoustic impedance is caused by the protective layer 112a, which is typically made from a polymer based material. In this embodiment, the protective layer 112a has a thickness that is less than that of a length of a wavelength of the acoustic energy being transmitted from the sensor 110.

The sensor 110 is designed to detect and measure acoustic impedance that is encountered by acoustic energy that it, the sensor 110 transmits. Such acoustic impedance is measured at a resolution of typically, hundreds of pillars (dots) per inch. In one embodiment, the sensor 110 is designed to detect acoustic impedance at 350 pillars (dots) per inch, via the matrix of vibrating pillars 116, generating acoustic energy at a 10 MHz frequency. In another embodiment, the sensor 110 is designed to detect acoustic impedance at 500 pillars (dots) per inch, via a higher density matrix of pillars, generating acoustic energy at about a 15 MHz frequency.

A lower surface of the finger 130 includes a finger print pattern that is comprised of many ridges and valleys (not entirely shown here). The finger 130 is in physical contact with the outer and upper surface of the sensor 110. For exemplary purposes, the lower surface of the finger 130 is shown here to have a surface topology that includes a fingerprint valley 132, and a fingerprint ridge 132a and a fingerprint ridge 132b. The fingerprint ridges 134a-134b are each adjacent to and surround the fingerprint valley 132. A fingerprint ridge 134a-134b causes a significantly higher amount of acoustic impedance to the flow of acoustic energy than that caused by a fingerprint valley 132.

The sensor 110 is designed to detect acoustic impedance associated with outside material that is located within the acoustic transmission path above each pillar (also referred to herein as dot) physically residing within the matrix of pillars 116. Each pillar also electrically resides within at least one electrical circuit that is embedded within the sensor 110.

Each pillar is made from piezo-electric material and is designed to mechanically oscillate in response to an electrical signal that it receives from the electrical circuit that it resides within. The resulting oscillation of each pillar transmits acoustic energy. The acoustic energy is transmitted in directions that are parallel or near parallel to a long dimension of each pillar.

In this configuration of the sensor 110, the long dimension of each of the pillars 116 is parallel to a vertical direction as shown, and as a result, acoustic energy is mostly transmitted simultaneously in an upward and in a downward direction as shown. Acoustic energy that is transmitted towards the downward direction passes through the lower protective barrier 112b, and then reflects off of or is transmitted through, a section of backing material 114. The backing material is designed to reflect almost all of the acoustic energy upwards and back into the sensor 110.

The transmission of acoustic energy is affected by, and the mechanical movement of each pillar is affected by, by acoustic impedance caused by material that resides along a transmission pathway through which the sensor generated acoustic energy is transmitted. Like the electrical signal driving the mechanical oscillation of each pillar, the acoustic impedance encountered along the transmission pathway also affects the rate and amplitude of oscillation of each pillar, which affects the electrical impedance caused by each pillar within the electrical circuit that it resides within. As a result, the amount of acoustic impedance encountered correlates with an electrical impedance value that is measured within the electrical circuit that is associated with the mechanical movement of each pillar.

Furthermore, the sensor 110 is designed to capture a two dimensional electronic map of acoustical impedance associated with and caused by the fingerprint at a resolution of at least 350 dots per inch. Such a map is captured via a digitizer, which is an electronic component operating inside of the sensor 110. Such a map of acoustical impedance can be translated into a map of the fingerprint itself. However, this finger print map is most accurate when the finger print is in direct physical contact with the sensor 110.

Acoustic impedance is measured in units of Rayls. An acoustic impedance property value of air is about 400 Rayls, and an acoustic impedance property value of a valley within a finger tissue of a fingerprint pattern is approximately the same as that of air, which is about 400 Rayls. An amount of acoustic impedance caused by a ridge within a fingerprint pattern is typically about 1.5 MRayls. An exact amount and difference between an amount of acoustic impedance caused by a valley and ridge varies from person to person. Typically, a fingerprint pattern ridge causes more than twice the amount of acoustic impedance as caused by a valley, within a fingerprint pattern of a person. In this embodiment, the amount of acoustic impedance residing within the sensor 110 as a whole, by itself, based upon the properties and the amount and arrangement of materials within the sensor, is about 20.36 MRayls.

There is a substantial difference between the acoustic impedance value of the sensor 110 in relation to that of finger tissue, and more specifically to either a fingerprint valley 132 or a fingerprint ridge 134a-134b of the finger tissue 130. This acoustic impedance property value difference is referred to herein as an acoustic impedance (AI) mis-match, and this AI mis-match between the sensor 110 and the finger tissue 130 factors into a computation of a reflection co-efficient (R), that indicates that more than 99% of the acoustic energy (AE) that is transmitted upward by the sensor 110 is actually reflected back into the sensor 220, at the boundary between the sensor 110 and the finger tissue 130, and as a result, only a small amount of the acoustic energy actually transmitted by the sensor actually reaches to or into the finger tissue 130.

Despite only a small amount of acoustic energy being transmitted into the finger tissue 130 by the sensor 110, electronic signal processing enables the sensor 110 to distinguish between a fingerprint valley 132 and a fingerprint ridge 134a-b. The sensor's ability to distinguish is based upon the relatively small difference in the respective acoustic impedance values between a valley 132 and a ridge 134a-134b.

Figure 2:
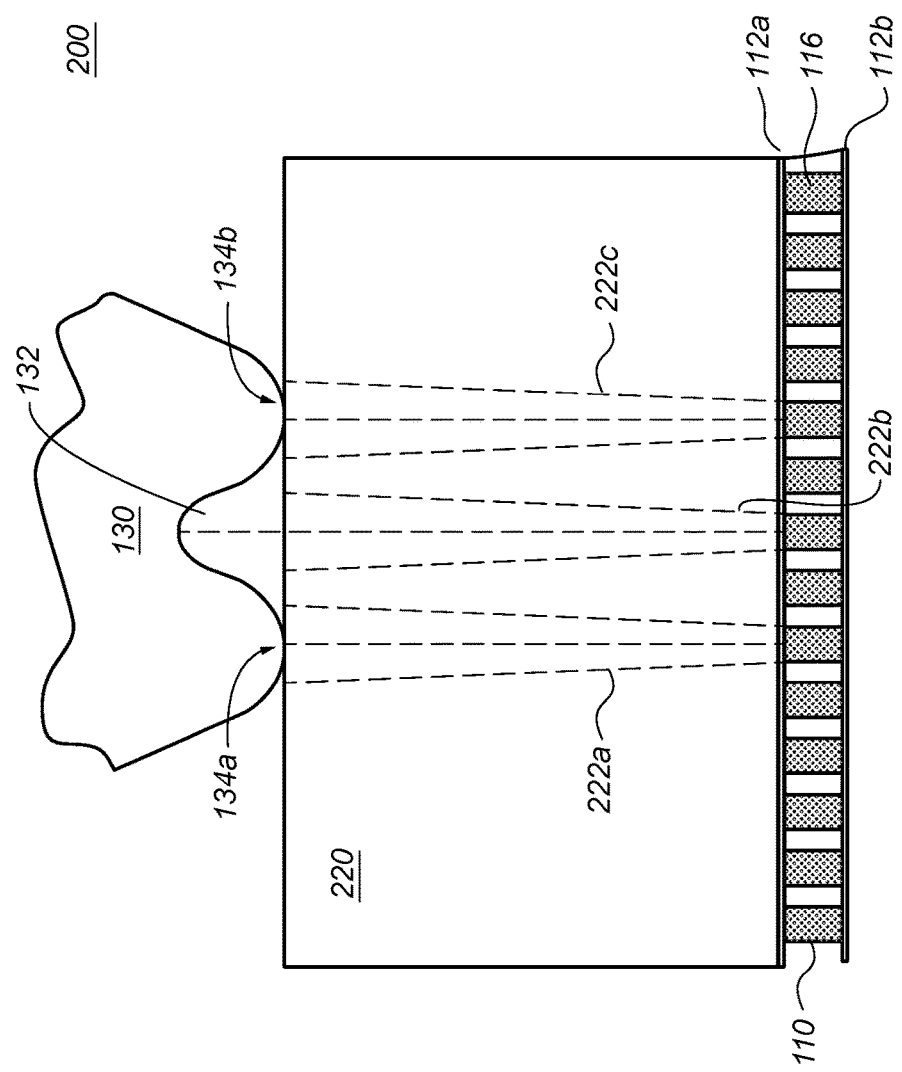
FIG. 2 illustrates an embodiment of an acoustic sensor of FIG. 1 that senses characteristics of the finger, while the finger is instead separated from the sensor by a barrier.

However, in other circumstances where another object, for example, a barrier is inserted between the sensor 110 and the finger 130, such as that shown in FIG. 2., disturbances, such as caused by other sources of acoustic impedance in addition to that from a fingerprint pattern and/or caused by additional reflections, refraction, diffusion and/or scattering of acoustic energy, can interfere with and degrade accurate sensor detection and measurement of acoustic impedance caused by a fingerprint pattern only, and as a result, can degrade accuracy of a determination of the presence and surface characteristics of a fingerprint ridge 134a-134b or valley 132 pattern of the finger tissue 130 being sensed by the sensor 110.

FIG. 2 illustrates an embodiment of an acoustic sensor 110 of FIG. 1 that senses characteristics of the finger 130, while the finger 130 is instead separated from the sensor 110 by a barrier 220. This type of embodiment (sensor configuration) can be useful where a barrier 220 can be employed to shield the sensor 110 from outside objects and/or to embed a sensor 110 into another device. For example, a barrier can function to embed an acoustic sensor into a mobile telephone, for example.

In this embodiment, the sensor 110 is about 100 microns in thickness as measured between its upper outer surface and its lower outer surface. The upper surface of the sensor, which is constituted by its upper protective layer 112a, abuts the lower side of the barrier 220, while the lower surface of the sensor 110, which is constituted by its lower protective layer 112b, abuts backing material 114 (Shown in FIG. 1). As an example, the thickness of the exemplary barrier 220 is about 700 microns as measured between its upper surface and its lower surface. The barrier 220 has a thickness of about (7) times greater than the thickness of the sensor 110. Other barriers made from different materials and having different dimensions can be employed within the scope of and in accordance with the invention.

As shown, when the sensor is operating, each pillar 116 vibrates and transmits acoustic energy towards a target 130, which in this circumstance, is a finger 130 including finger tissue 130. The finger tissue 130 has a lower surface upon which a fingerprint pattern is located. Within this fingerprint pattern, there is located an exemplary fingerprint valley 132 that is surrounded on its left and right hand side respectively, by two fingerprint ridges 134a-134b.

Each vibrating pillar transmits acoustic energy that is represented as a beam of acoustic energy 222a-222c. Note that each beam of acoustic energy is transmitted from a vibrating pillar that vibrates in accordance with a frequency, amplitude and power. Each beam of acoustic energy has a width dimension. This width dimension varies as a function of the distance of the beam from its source of transmission.

As shown, the width dimension of the beam increases as a function of its distance from the sensor 110, which is the location from which transmission of each beam originates. This effect is also referred to herein as a beam widening effect. Note that this beam widening effect is an inverse function of the frequency of each acoustic energy beam, meaning that an acoustic energy beam narrows as a function of its rising frequency. As shown, the beam appears to have sort of an upside down cone shape. There is a benefit to transmitting a higher frequency acoustic energy beam given that a higher frequency, and narrower beam having a narrower cone shape, can be employed by the sensor 110 to yield a higher resolution image. Essentially, the resulting narrower beam is focused onto a smaller area of a target 130 that is located at the boundary between the target 130 and the upper surface of the barrier 220.

Note that detection and measurement of acoustic impedance from a particular source of acoustic impedance, where that source is a particular distance away from the sensor 110, is dependent upon timing of such an acoustic impedance measurement in relation to when acoustic energy was transmitted as a prerequisite to perform such a measurement. The farther away a source of acoustic impedance is from the transmitting sensor 110, the more time is required after transmission to measure an amount of acoustic impedance that is caused by that source. As a result, the timing of acoustic measurements can be calculated to focus on measuring acoustic impedance that is located along a plane that is a fixed distance from the sensor 110. Such a plane can intersect a fingerprint pattern that is located just above the upper surface of the barrier 220.

In some embodiments, acoustic energy is transmitted via a series (line) of vibrating transmission pillars, while acoustic impedance is simultaneously measured via another one or more series (lines) of reception pillars, which are preferably arranged orthogonal to the series of transmission pillars. The sensor 110 can control timing of the reception/signal processing of the reception lines to focus on acoustic impedance along a plane as described above, and that is located at a particular distance from the sensor. This concept is also referred to as transmitting and receiving a "sum delayed beam".

Empirical observations of a prototype system like the configuration described herein reveal that the presence of this barrier 220 causes a substantial reduction in the image quality and resolution of any fingerprint pattern image that is attempted to be sensed (acoustic impedance scanned) by the sensor 110 through this barrier 220, as compared to the acoustic impedance scanning of the same fingerprint pattern via the barrier-less sensor configuration of FIG. 1.

However, additional experimentation and further empirical observations reveal that this substantial reduction in image quality and resolution can be substantially (mostly) eliminated if and when the sensor 110 and/or the barrier 220 is modified to possess an acoustic impedance property value that is equal or near equal to each other, and if an electrical signal that drives pillar vibration is raised to frequency above a resonance frequency of the sensor 10, where the resonance frequency would be present (in effect) if the sensor was operating with no barrier 220, and if signal processing activity for measuring acoustic impedance is modified to be performed within a narrowly defined window in time.

In this barrier configuration, for example, the barrier 220 is made from Gorilla glass, which possesses an acoustic impedance property of about 16 MRayls (16 million Rayls). The amount of acoustic impedance caused by the barrier 220 (16 MRayls) is much larger than the amount of acoustic impedance caused by either a valley 132 (400 Rayls equaling 0.0004 MRayls) or caused by a ridge 134a-134b (1.5 MRayls), that reside within a fingerprint pattern and along the outer surface of finger tissue 130.

In this embodiment, the acoustic impedance caused by the sensor 110 itself, is about 20.36 MRayls, which is different and somewhat larger than the 16 MRayl rating of the barrier 220, causing a 4+ MRayl acoustic impedance mis-match between the sensor 110 and the barrier 220.

The amount of acoustic impedance caused by the barrier 220 is somewhat independent of the thickness of the barrier 220 itself, and as a result, a thinner barrier made from Gorilla glass would not be expected, by itself, to substantially reduce the acoustic impedance mis-match between the barrier 220 and the sensor 110, and as a result, not likely to improve the sensor 110 accuracy for distinguishing a valley and a ridge, within a fingerprint pattern of finger tissue 130 making physical contact with the upper surface of the barrier 220.

Figure 3:
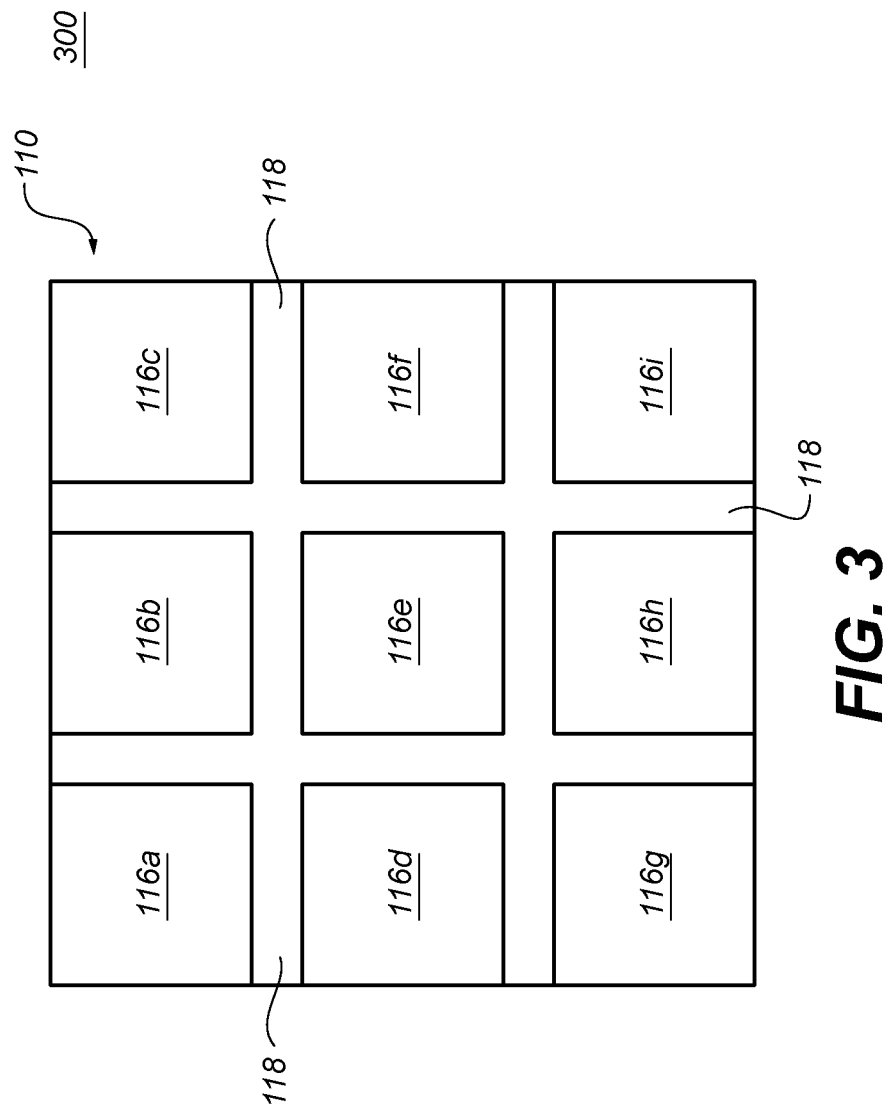
FIG. 3 illustrates an embodiment of an acoustic sensor that is capable of more accurate sensing of the characteristics of the finger, while the finger is separated from the sensor by the barrier of FIG. 2.

As will be further described in association with FIG. 3, the sensor itself 110 has an effective acoustic impedance property value 20.36 MRayls, as compared to that (16 MRayls) of the barrier 220. As a result, there is no exact match of acoustic impedance property values between the sensor 110 and the barrier 220.

In theory, and in accordance with the reflection coefficient (R), there should be no reflection of acoustic energy that is transmitted from the sensor 110 through the barrier 220, if the acoustic impedance of the sensor 110 exactly matches that of the barrier 120. Also, an acoustic impedance mismatch causes increased reflection of acoustic energy being transmitted from the sensor 110 by the barrier 220, as compared to the circumstance where there is an exact acoustic impedance match between the sensor 110 and the barrier 220.

In accordance with computation of the reflection coefficient (R), the (20.36–16 MRayl) mismatch between the sensor 110 and the barrier 220 causes less than 2% of acoustic energy that is transmitted from the sensor 110 towards the barrier 220, to be reflected back towards the sensor 110. However, despite there being only less than 2% reflection of acoustic energy, experimental results show that substantial reduction in image quality occurs with such an (20.36–16) MRayl) acoustic impedance mismatch between the sensor 110 and the barrier 220.

FIG. 3 illustrates a top-down view of the internal geometry of a sub-section of the pillar matrix of the acoustic sensor 110 of FIGS. 1-2. As shown, a sub-matrix of (9) pillars 116a-116i each have a 40 by 40 micron cross-section. The interstitial material 118 is 10 microns in width between each pillar 116. Each pillar is made from a piezo-ceramic material having an acoustic impedance property value of 27 MRayls, and has a 1600 square micron cross-sectional area size. The interstitial material has an acoustic impedance property value of 2 MRayls and has a total 5200 square micron cross-sectional area size. Hence, computing a weighted average of the acoustic impedance of each material type in proportion to the amount of its cross-sectional area, the effective acoustic impedance of the sensor sub-section, and that of the sensor 110 in its entirety, is 20.36 MRayls.

Figure 4:
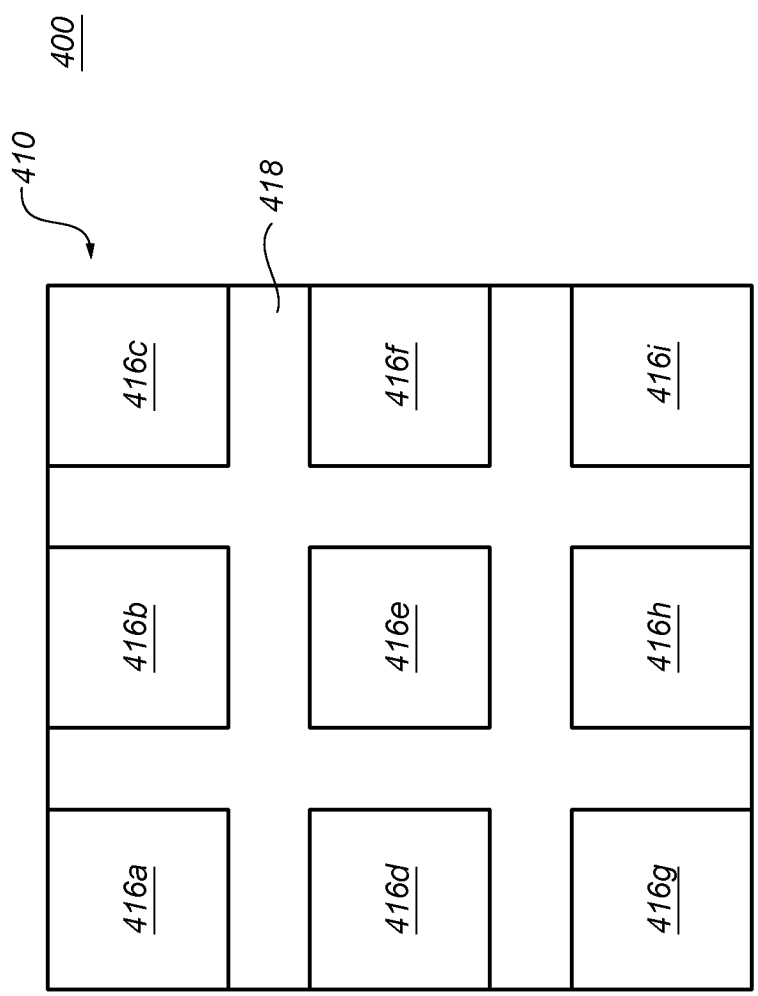
FIG. 4 illustrates a top-down view of a modified internal geometry of a sub-section of the pillar matrix of the acoustic sensor of FIGS. 1-2, to create an acoustic impedance matched sensor.

FIG. 4 illustrates a top-down view of a modified internal geometry of a sub-section of the pillar matrix of the acoustic sensor of FIGS. 1-2, to create an acoustic impedance matched sensor 410. As shown, each of the pillars 416a-416i have a cross-sectional area of 35×35 microns in dimension.

In accordance with the invention, and as shown, the cross-sectional geometry of FIG. 3 can be modified to alter the overall effective acoustic impedance of the sensor 110 of FIGS. 1-3. For example, if the cross-sectional area of the pillars 116 of FIG. 3 was each instead reduced from a 40×40 micron cross-section, to a 35×35 micron cross-section, and the amount of interstitial material between the pillars was increased from 10 microns to 20 microns in width, to fill in for the reduced size of the cross-section of each pillar 116, the size of the this sub-section would remain the same, however the acoustic impedance of this modified sensor sub-section, and that of the sensor 110 as a whole, would be reduced to about 16.06 MRayls, which would nearly match that of the barrier 220, and would contribute to a substantial improvement to the sensor scanned image quality and resolution.

Further, modifications to the ceramic composition of the pillars 116 can further adjust the acoustic impedance property value of the ceramic material of the pillars, which could enable in a practical manner, a closer and more exact acoustic impedance match between the modified sensor 410 to the barrier 220, which contributes to yielding experimentally verified best image quality and resolution when scanning a fingerprint pattern through barrier 220.

Figure 5:
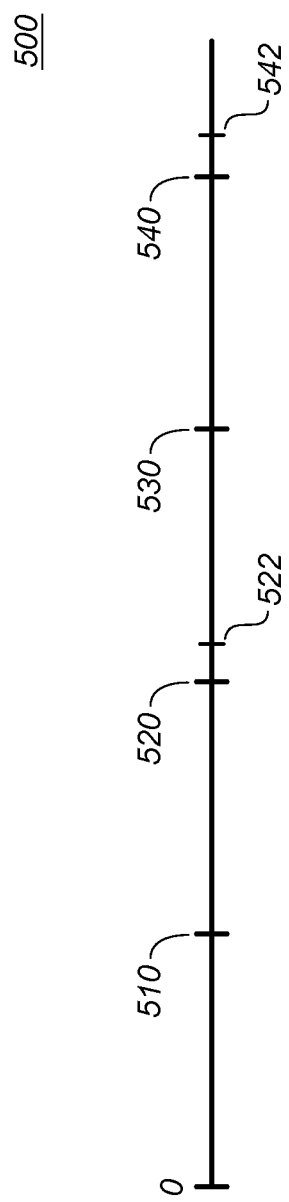
FIG. 5 illustrates measurement (gating) time windows that better enable more accurate measurement of acoustic impedance by the modified sensor 410 through the barrier of FIG. 2.

FIG. 5 illustrates measurement (gating) time windows that better enable more accurate measurement of acoustic impedance that is detected by the modified sensor 410 through the barrier of FIG. 2.

Experimental results further show that modified signal processing in accordance with these measurement (gating) time windows, contributes to further enhancing the quality and resolution of acoustically scanned images.

In accordance with the invention, while in operation, the sensor 410 transmits an acoustic energy pulse, typically of 10 microseconds in duration, upwards and towards the finger tissue 130 through the barrier 220. The signal processing hardware of the sensor 410 is configured to perform a measurement of the sensed acoustic impedance, in association with each pillar, starting at a time when the pulse reflects off of the boundary between the upper surface of the barrier 220 and a target, such as finger tissue 130 and/or air, or other object above the barrier 220, and the acoustic energy pulse returns, round trip, back to the sensor 410. The aforementioned boundary, is also referred to herein, as the upper boundary of the barrier 220.

Importantly, matching the acoustic impedance property values between the sensor 410 and the barrier 220 yields another advantage in that it reduces a resonance effect within the sensor 410. The resonance effect is a phenomenon that occurs when an electrical signal frequency, that is driving the mechanical pillar vibration, causes the amplitude of pillar vibration to substantially increase (spike) at a particular resonance frequency. The resonance frequency is associated with a mechanical portion of the sensor 110, 410 as a whole, which is the design, material properties and geometry of a matrix of pillars and the interstitial material disposed between those pillars, and the upper and lower protective layers 112a-112b.

For example, in an embodiment of the sensor 110, resonance occurs at a pillar driving signal frequency of about 15 MHz, when the sensor 110 is in direct contact with a target such as finger tissue 130 and/or air, and is not abutting any barrier. However, when that same embodiment of the sensor is impedance matched with a barrier, then resonance will not occur at a 15 MHz pillar driving signal frequency.

Instead, in this circumstance, experimental results indicate that the pillar driving signal frequency can be raised to over 20 MHz, which is about another 40 percent above the prior existing 15 MHz resonance frequency, and without resonance occurring within the sensor. Such a higher pillar driving signal frequency causes a narrower acoustic energy beam to be transmitted from a pillar 116 towards a target, increasing acoustic impedance measured image resolution.

Pillar vibration amplitude gain by a factor of 5-6 is can occur when pillars 116 are vibrating at a pillar driving frequency causing resonance. Such pillar vibration amplitude gain does not occur outside of resonance. Such lack of lack of pillar vibration amplitude gain outside of resonance, can be at least partially compensated for, by increasing signal voltage of the pillar driving signal outside of resonance. For example, during experimentation, the pillar driving signal voltage has been increased to about a factor of three outside of resonance, as compared to the pillar driving signal voltage normally employed inside of resonance, which accordingly increases pillar vibration amplitude outside of resonance by about a factor of three.

Experimental results show that fingerprint pattern acoustic impedance scanning improvements can be achieved when matching the sensor and barrier to within about 10 percent of each other. However, further improvements are realized with closer acoustic impedance matching is achieved, and it is expected that best improvements are expected to be achieved with near and exact matching, however challenging that is to practically achieve.

Also note that, the amplitude of pillar vibration substantially reduces at driving frequencies that are slightly above or below that particular resonance frequency, associated with the mechanical portion of the sensor as a whole.

Note that the mechanical portion of the sensor as a whole, which includes pillars and interstitial material that abut and attach to each other in a manner that forms one stiff object in combination. This stiff object in combination, being a mechanical portion of a sensor 110, 410, has one measurable acoustic impedance property value associated with it.

When acoustic impedance matching the sensor 410 with the barrier 220, the resonance effect subsides, substantially eliminating the above described vibration amplitude spike, and enabling electrical driving frequencies to raise to a frequency above any resonance frequency that would otherwise be in effect (exist) without such acoustic impedance matching between the sensor 110 and the barrier 220, which would occur in circumstances when the sensor 110, 410 was in direct physical contact with a target, such as in direct physical contact with finger tissue 130 and/or air, and not in direct physical contact with a barrier. As a result, the electrical driving signal can be raised far higher than the resonance frequency in circumstances having such impedance matching between the sensor 410 and the barrier 220, for example, for example, 10 Megahertz higher than the resonance frequency in circumstances without such acoustic impedance matching, yielding higher image resolution for sensor 410 scanned fingerprint pattern images.

Referring again to FIG. 5, time marker 510 represents the time required for a sensor transmitted acoustic energy pulse to travel from the sensor 110, into the barrier 220 and to reflect off of the upper boundary of the barrier 220. This is event is referred to herein as a first pulse reflection occurring at time marker 510. For the exemplary embodiment of the barrier 220 herein, being about 700 microns thick and made from Gorilla glass, this first acoustic pulse reflection occurs at about 70 nanoseconds after an initial transmission of the acoustic energy pulse from the sensor 410 through the barrier 220.

Time marker 520 represents a round trip time for the acoustic energy pulse to travel from the sensor 410, into the barrier 220 and to reflect off the upper boundary of the barrier, which is the boundary between the upper surface of the barrier 220 and a target, such as the finger tissue 130 and/or air, and then to return to the sensor 410.

In this embodiment of the barrier 220, the speed of sound through the Gorilla glass of the barrier travels at about 5800 meters/second, which is faster than the speed of sound traveling through air. For this particular embodiment of the barrier 220, the round trip reflection for the acoustic energy pulse requires about 140 nanoseconds to be transmitted from the sensor 410, and then reflect off of the boundary between the upper surface of the barrier 220, and then return back to the sensor 410.

Time marker 522 represents a time when acoustic energy that is transmitted in a downward direction from the sensor 410, and that reflects upward off of the sensor backing 114, and then travels back through the sensor 410 and into the barrier 220, and then reflects off the upper boundary surface of the barrier 220, and returns to the sensor 410.

For this embodiment of the sensor 410 and barrier 220, this time marker 522 occurs about 60 nanoseconds after time marker 520. However, this amount of time is dependent upon the dimensions and the speed of sound through the particular embodiment of the sensor. As for time marker 530, this time marker represents an additional 70 nanoseconds after time marker 520, and time marker 540 represents additional 70 nanoseconds after time marker 530. As for time marker 542, it represents a second reflection back to the sensor 410 from the acoustic energy transmitted downward by the sensor 410, and it occurs about 60 nanoseconds after time marker 540.

Experimental results further show that measurement of acoustic impedance is most accurately performed between time markers 520 and 540 for the herein described combination of the sensor 110 and barrier 220. Measurement is generally less accurately performed prior to time marker 520 and after time marker 540. This period of time is between 520 and 540 is also referred to herein as a favorable (accurate) measurement (gating) time window for measuring acoustic impedance associated with each pillar 116, in accordance with the herein described particular embodiment of the sensor 110 and barrier 220 that are described herein to operate together.

The exact timing and size of this gating time window will vary if and when either a different barrier and/or different sensor are combined to operate together. In these other circumstances, the exact timing and size of this gating time window will be determined in accordance with the disclosure of the invention herein, and will depend upon the particular embodiment (design and dimensions and material) of the sensor and barrier, and upon the resulting speed of sound within each of the sensor and barrier, that are combined to operate together in some other hypothetical embodiment of a sensor and barrier combination.

In some embodiments, an acoustic impedance measurement (sample) can be performed within a time period of 20 nanoseconds, depending upon the design of the digitizer component and the scheme for measuring acoustic impedance for each pillar 116.

Hence, multiple acoustic impedance (AI) measurements can be performed within the above described measurement (gating) time window, for the purpose of comparison and selection of sample measurement results. In some circumstances, performing multiple AI measurement samples can improve accuracy and improve image quality and resolution, as compared to performing one and only one AI measurement sample. The experimental results also show that acoustic energy sample measurements are best performed as early as possible within this time window starting at time marker 520.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for acoustically scanning a target, comprising:
   a barrier having an acoustic impedance property value and having a first side and a second side that each face in substantially opposing directions; and
   an acoustic sensor having an acoustic impedance property value that matches or proximately matches said acoustic impedance value of said barrier, said acoustic sensor having a first transmitting side through which acoustic energy is transmitted away from said acoustic sensor, wherein said first transmitting side of said acoustic sensor is positioned so that it abuts said first side of said barrier, and positioned so that said acoustic sensor is configured to transmit said acoustic energy through said barrier and towards a target abutting said second side of said barrier, said acoustic sensor is configured to measure acoustic impedance of said target within a measurement time window while simultaneously transmitting said acoustic energy, wherein said measurement time window initiates following an initial transmission of acoustic energy from said acoustic sensor, and terminates no later than upon an occurrence of two round trip travel times, and each said round trip travel time is an amount of time required for said acoustic energy to transmit from said acoustic sensor to said target and to reflect from said target and arrive back to said acoustic sensor.

2. The apparatus of claim 1, wherein said measurement time window instead initiates after an occurrence of one said round trip travel time after said initial transmission of acoustic energy from said acoustic sensor occurs.

3. The apparatus of claim 1, wherein said measurement time window terminates after an occurrence of one said round trip travel time after said initial transmission of acoustic energy from said acoustic sensor to said target and return to said acoustic sensor.

4. The apparatus of claim 1, wherein said acoustic impedance property value of said acoustic sensor proximately matches that of said barrier by having an amount of acoustic impedance that is no more than two percent different from said acoustic impedance property value of said barrier.

5. The apparatus of claim 1, wherein said acoustic impedance property value of said acoustic sensor proximately matches that of said barrier by having an amount of acoustic impedance that is no more than five percent different from said acoustic impedance property value of said barrier.

6. The apparatus of claim 1, wherein said acoustic impedance property value of said acoustic sensor proximately matches that of said barrier by having an amount of acoustic impedance that is no more than ten percent different from said acoustic impedance property value of said barrier.

7. The apparatus of claim 1, wherein said acoustic sensor includes an acoustic energy transmitter, which has a rear side that abuts a backing material having a substantially lower acoustic impedance property value relative to that of said barrier.

8. The apparatus of claim 7, wherein said substantially lower acoustic impedance property value is no more than ten percent of that of said acoustic sensor.

9. The apparatus of claim 7, wherein said substantially lower acoustic impedance property value is no more than two percent of that of said acoustic sensor.

10. The apparatus of claim 7, wherein said backing material is air.

11. The apparatus of claim 1, wherein said acoustic energy is transmitted at a frequency exceeding a resonant frequency for said acoustic sensor that would otherwise be in effect if said acoustic sensor was instead being operated in direct physical contact with said target.

12. The apparatus of claim 1, wherein said acoustic energy is transmitted at a frequency of at least 10 Mhz.

13. The apparatus of claim 1, wherein said acoustic energy is transmitted at a frequency of at least 18 Mhz.

14. A system for acoustically scanning a target, comprising:

a barrier having an acoustic impedance property value and having a first side and a second side that each face in substantially opposing directions;

an acoustic sensor having an acoustic impedance property value that matches or proximately matches said acoustic impedance value of said barrier, said acoustic sensor having a first transmitting side through which acoustic energy is transmitted away from said acoustic sensor, wherein said first transmitting side of said acoustic sensor is positioned so that it abuts said first side of said barrier, and positioned so that said acoustic sensor is configured to transmit said acoustic energy through said barrier and towards a target abutting said second side of said barrier, said acoustic sensor is configured to measure acoustic impedance of said target within a measurement time window while simultaneously transmitting said acoustic energy, wherein said measurement time window initiates following an initial transmission of acoustic energy from said acoustic sensor, and terminates no later than upon an occurrence of two round trip travel times, and each said round trip travel time is an amount of time required for said acoustic energy to transmit from said acoustic sensor to said target and to reflect from said target and arrive back to said acoustic sensor; and a backing material in contact with a second side of said acoustic sensor.

15. The system of claim 14, wherein said measurement time window instead initiates after an occurrence of one said round trip travel time after said initial transmission of acoustic energy from said acoustic sensor.

16. The system of claim 14, wherein said acoustic energy is transmitted at a frequency exceeding a resonant frequency for said acoustic sensor that would otherwise be in effect if said acoustic sensor was instead being operated in direct physical contact with said target.

17. A method for acoustically scanning a target, comprising:

providing a barrier having an acoustic impedance property value and having a first side and a second side that each face in substantially opposing directions;

positioning an acoustic sensor having a first transmitting side through which acoustic energy is transmitted away from said acoustic sensor, wherein said acoustic sensor is positioned such that it abuts said first side of said barrier, and an acoustic impedance property value of said acoustic sensor matches or proximately matches said acoustic impedance value of said barrier;

transmitting said acoustic energy from said acoustic sensor through said barrier and towards a target abutting said second side of said barrier; and measuring acoustic impedance of said target at said acoustic sensor within a measurement time window while simultaneous transmission of said acoustic energy from said acoustic sensor, wherein said measurement time window initiates following an initial transmission of acoustic energy from said acoustic sensor, and terminates no later than upon an occurrence of two round trip travel times, and each said round trip travel time is an amount of time required for said acoustic energy to transmit from said acoustic sensor to said target and to reflect from said target and arrive back to said acoustic sensor.

18. The method of claim 17, wherein said measurement time window instead initiates after an occurrence of one said round trip travel time after said initial transmission of acoustic energy from said acoustic sensor.

19. The method of claim 17, wherein said acoustic impedance property value of said acoustic sensor is within two percent of said acoustic impedance property value of said barrier.

20. The method of claim 17, wherein said acoustic energy is transmitted at a frequency exceeding a resonant frequency for said acoustic sensor that would otherwise be in effect if said acoustic sensor was instead being operated in direct physical contact with said target.

* * * * *